United States Patent [19]

Boreskov et al.

[11] 4,130,570
[45] Dec. 19, 1978

[54] METHOD OF PRODUCING ETHYLENE OXIDE

[76] Inventors: Georgy K. Boreskov, Zolotodolinskaya ulitsa, 85; Mikhail G. Slinko, ulitsa Voevodskogo, 2, both of Novosibirsk; Anatoly I. Gelbshtein, ulitsa Fersmana, 11, kv. 76, Moscow; Lidia A. Vasilevich, 2 Sovetskaya ulitsa, 6, kv. 27, Moscow; Boris B. Chesnokov, Malaya Filevskaya ulitsa, 16, kv. 54, Moscow; Irina T. Frolkina, Khokhovsky pereulok, 11, kv. 40, Moscow; Oskar N. Dyment, 6 Parkovaya ulitsa, 12/1, kv. 70, Moscow; Jury N. Stepanov, shosse Entuziastov, 192, kv. 33, Moscow; Valery A. Davydov, Nalesny pereulok, 15/7, kv. 3, Moscow; Irina G. Talaeva, ulitsa Partizanskaya, 18, korpus 2, kv. 3, Moscow; Ninel S. Utkina, ulitsa Izumrudnaya, 32, kv. 23, Moscow; Vera V. Stroganova, ulitsa Karla Marxa, 34, Ljubertsy Moskovskoi oblasti; Maria S. Aksenova, ulitsa Gerasima Kurina, 8, korpus 2, kv. 53, Moscow, all of U.S.S.R.; Anna G. Filippova, deceased, late of Moscow, U.S.S.R.; by Olga B. Prosvirova, administrator, Uralskaya ulitsa, 17, kv. 169; by Irina B. Zakharova, administrator, 11 Parkovaya ulitsa, 44, korpus 3, kv. 123, both of Moscow, U.S.S.R.

[21] Appl. No.: 613,806
[22] Filed: Sep. 16, 1975

Related U.S. Application Data

[63] Continuation of Ser. No. 407,837, Oct. 19, 1973, abandoned.

[51] Int. Cl.$^2$ ............................................. C07D 301/22
[52] U.S. Cl. ................................................ 260/348.35
[58] Field of Search .................... 260/348.5 F, 348.35

[56] References Cited

U.S. PATENT DOCUMENTS

| | | | |
|---|---|---|---|
| 2,752,363 | 6/1956 | Drummond et al. | 260/348.5 F |
| 3,332,887 | 7/1967 | Endler | 252/443 |
| 3,785,561 | 1/1974 | Slinko | 260/348.5 F |

FOREIGN PATENT DOCUMENTS

| | | | |
|---|---|---|---|
| 560782 | 7/1958 | Canada | 260/348.5 F |
| 1117096 | 11/1961 | Fed. Rep. of Germany | 260/348.5 R |
| 591670 | 8/1947 | United Kingdom. | |

*Primary Examiner*—Norma S. Milestone
*Attorney, Agent, or Firm*—Holman & Stern

[57] ABSTRACT

The invention relates to a method of producing ethylene oxide, consisting in that ethylene is oxidized with oxygen or air in a fluidized bed of a silver catalyst containing cadmium carbonate and/or cadmium oxide and also fused alumina having a particle size of between 2 microns and 0.5 mm, the components of the catalyst being taken in the following proportion (wt.%): silver, between 9.5 and 76; cadmium carbonate and/or cadmium oxide, between 0.5 and 4 (in terms of metallic cadmium); fused alumina, between 90 and 20. The oxidation of ethylene takes place at a partial pressure of ethylene between 0.6 and 15 atm, a partial pressure of oxygen between 0.1 and 2 atm, at an aggregate pressure of 2 to 20 atm and a temperature between 200° and 300° C in a reactor with a packing. The fused alumina may be used as a filler or support. In order to improve the selectivity of the process, it is preferable to use a silver catalyst containing, in addition to with the above components, silver chloride in an amount of between 0.03 and 0.3% of the weight of the silver present in the catalyst. The catalyst used in the disclosed process is characterized by high selectivity and stability in operation, providing for high productivity of the process. Said catalyst and the conditions under which the process of ethylene oxidation takes place provide for an efficient and economically-attractive method of producing ethylene oxide on an industrial scale.

17 Claims, No Drawings

METHOD OF PRODUCING ETHYLENE OXIDE

This is a continuation of application Ser. No. 407,837, filed Oct. 19, 1973 and now abandoned.

BACKGROUND OF THE INVENTION

The present invention relates to methods of producing ethylene oxide by the catalytic oxidation of ethylene. Ethylene oxide ranks high among other products of organic synthesis in terms of the tonnage turned out, the wide-spread application enjoyed in the manufacture of antifreeze, man-made fibres, surfactants, etc. along with the derivatives of ethylene oxide, such as ethylene glycol, ethers of ethylene glycol, ethynol amine, etc.

Methods of producing ethylene oxide are known in the art by the oxidation of ethylene with oxygen or air at a temperature between 200° and 300° C. in a fluidized bed of a silver catalyst containing an oxide of a metal from the second group of the periodic table, such as barium or calcium, deposited on a support which may be fused alumina, mullite (aluminium silicate refractory) or Carborunbum.

The known methods suffer from a number of disadvantages, such as low hourly rate of output (between 60 and 100 g of ethylene oxide per liter of catalyst), an inadequately high catalyst strength, as their tendency is to coalesce when in fluidized state, and low concentration of ethylene oxide in the feed stream. In large diameter reaction vessels used for oxidation the selectivity and conversion are low due to the impaired homogeneity of the fluidized bed and the fact that some of the reaction gas passes through this bed in large bubbles interfering with both mass and heat transfer.

SUMMARY OF THE INVENTION

It is an object of the present invention to provide an efficient and economically attractive method of producing ethylene oxide on an industrial scale characterized by high selectivity and stability of catalyst and a high rate of output.

In accordance with said and other objects, the invention consists in that ethylene is subjected to oxidation with oxygen or air in a fluidized bed of a silver catalyst containing cadmium carbonate and/or cadmium oxide and also fused alumina with a particle size between 2 microns and 0.5 mm, the components of the catalyst being taken in the following proportion (wt.%): silver between 9.5 and 76, cadmium carbonate and/or cadmium oxide between 0.5 and 4 (based on metallic cadmium), fused alumina between 90 and 20. The oxidation of ethylene is conducted at a partial pressure of ethylene between 0.6 and 15 atm, a partial pressure of oxygen between 0.1 and 2 atm, at an aggregate pressure of from 2 to 20 atm and at a temperature of 200° to 300° C. in a reactor with a packing.

Due to the presence of cadmium carbonate and/or cadmium oxide in the catalyst along with fused alumina, the particles of silver do not coalesce, assuring thereby good fluidization of the catalyst pellets. The high partial pressure of ethylene and oxygen maintained throughout the process and also an aggregate pressure of between 2 and 20 atm provides for a high production rate and selectivity of the process. The presence of the packing in the reactor is a factor providing for the uniform fluidization thus enabling the reactor to operate under the conditions approaching those of ideal displacement of the gas and ideal mixing with the catalyst.

If the process is carried out in a large-diameter reactor, it is preferable to use one in which the packing is disposed between the cooling tubes accomodated in said reactor. An arrangement like this eliminates the problem of removing the heat of reaction liberated in appreciable amounts and provides for uniform fluidization at the same time, thus assuring thereby the high performance criteria of the process.

In order to increase the selectivity of the process it is of advantage to also use silver catalyst containing, an addition to the components referred to above, silver chloride in an amount of between 0.03 and 0.3% of the weight of the silver present in the catalyst.

The fused alumina incorporated into the catalyst may operate as a filler or support. In either case, its presence reduces the silver content of the catalyst, prevents the "dulling" of silver, eliminates agglomeration of the catalyst pellets and assures the requisite strength of catalyst.

If fused alumina performs the function of a filler, it is of advantage to use a silver catalyst containing fused alumina having a particle size of between 2 and 20 microns, the composition of the catalyst being as follows (wt.%): silver between 76 and 38, cadmium carbonate and/or cadmium oxide between 4 and 2 (based on metallic cadmium) and fused alumina between 20 and 60.

In order to increase the selectivity of the process it is preferable to also use a silver catalyst containing, along with the other components referred to above, silver chloride in an amount between 0.03 and 0.3% of the weight of the silver present in the catalyst.

In order to maximize the saving effect of the silver and improve the strength of catalyst, it is preferable to use a silver catalyst containing fused alumina as a support having a pellet size of between 0.1 and 0.5 mm, a porosity of from 25 to 45 vol % and a surface area of between 0.2 and 0.8 m$^2$/g, the components of the catalyst being taken in the following proportion (wt.%): silver between 9.5 and 19, cadmium carbonate and/or cadmium oxide between 0.5 and 1 (based on metallic cadmium), and fused alumina between 90 and 80.

The fused alumina used as the support can be prepared by pelletizing the fused alumina with a particle size of between 2 and 20 microns into pellets which are then subjected to calcination at 1600° to 1650° C.

In order to facilitate the process of pelletizing and to obtain a quality support, it is of advantage to add a 10- to 15-% aqueous solution of starch gum to the particulate fused alumina prior to pelletizing.

In order to keep the temperature of calcination at its lowermost level and to control the porous structure of the support, it is preferable to prepare the porous pellets from fused alumina having a particle size of between 2 and 20 microns mixed with ground glass with a particle size of between 5 and 40 microns in a proportion of between 3 and 10 to 1 particles by weight, respectively, and wetted with a 10- to 15-% aqueous solution of starch gum before calcining the pellets at a temperature between 1200° and 1400° C.

If the fused alumina is used as the support, it is of advantage to increase the selectivity of the process by using a silver catalyst also containing, along with the other components referred to above, silver chloride in an amount between 0.1 and 0.3% of the weight of the silver present in the catalyst.

The selectivity of the catalyst may be increased and it maintained unchanged for a protracted period of catalyst service, by preferably oxidizing ethylene in the presence of a chloride of sodium, potassium, lithium, barium or cadmium introduced into the fluidized bed of silver catalyst in an amount between 0.1 and 5% of the weight of the silver present in the catalyst.

In order to provide for a well-developed surface for the chlorides and, consequently, to engender a pronounced increase in catalyst selectivity, it is preferable to use said chlorides by applying them to a porous support which may be either fused alumina or Carborundum in pellets sized between 0.1 and 1 mm having a porosity of 25 to 45 vol % and a surface area of 0.2 to 0.8 m$^2$/g.

For promoting catalyst selectivity and maintaining it at a high level, it is better to pass the reaction gas mixture through a bed of a chloride of sodium, potassium, lithium, barium or cadmium present in an amount of at least 1 vol % at 100° to 300° C. before feeding the said mixture into the fluidized bed of silver catalyst, with said salts being utilized at this stage in an amount of between 0.5 and 5% of the weight of the silver present in the catalyst.

In order to provide for a well-developed surface for the chlorides and, consequently, for a pronounced increase in catalyst selectivity, it is preferable to apply the said chlorides to a porous support which may be either fused alumina or Carborundum in pellets sized between 0.1 and 10 mm with a porosity of 25 to 40 vol % and a surface area of from 0.2 to 0.8 m$^2$/g.

Furthermore, an invariably high catalyst selectivity is achievable through a protracted period of catalyst service if the reaction gas mixture is passed through pentachlorodiphenyl present in an amount of between 0.1 and 1 vol % at a temperature of from 50° to 150° C. before being introduced into the fluidized bed of silver catalyst.

For the purpose of maintaining the oxygen content of the reaction gas mixture at the maximum tolerable explosion-proof level, and increasing the yield of ethylene oxide and reducing the uneconomical consumption of ethylene, it is preferable to oxidize the ethylene in the presence of methane, the latter being under a partial pressure of between 0.5 and 10 atm and the ratio of methane-to-ethylene partial pressures being between 1:2 and 2:1, respectively.

In order to increase the oxygen content of the reaction gas mixture to the maximum tolerable explosion-proof level and to improve the yield of ethylene oxide, it is preferable to add more oxygen or air to the reaction gas mixture before feeding this mixture into the fluidized bed of silver catalyst, with the mixing taking place in vertical tubes disposed in the lower part of the reactor which is given a diameter which assures explosion-proof conditions for the mixing of said gases.

In order to create more hazard-proof conditions for the mixing of the reaction gas mixture with extra oxygen or air, it is preferable to fill the vertical tubes and the free space in the lower part of the reactor with a packing.

An increase in the oxygen content of the reaction gas mixture desirable for the purpose of increasing the productivity of the process can also be achieved by adding more oxygen or air to the reaction gas mixture in a bed of packing disposed in the lower part of the reactor to provide for explosion-proof mixing conditions of said gases before feeding said mixture to the fluidized bed of silver catalyst.

The method for producing ethylene oxide disclosed herein is embodied on the following lines of methodology.

Ethylene is oxidized with oxygen or air in a packed reactor at a temperature between 200° and 300° C. in a fluidized bed of silver catalyst under a partial pressure of ethylene between 0.6 and 15 atm, a partial pressure of oxygen between 0.1 and 2 atm and under an aggregate pressure of 2 to 20 atm. The process is accomplished in a recycle system with the addition of fresh ethylene and oxygen to the recycling gas mixture and with bleeding some of the gas mixture to prevent the accumulation of non-reactants (nitrogen, argon and the like).

During the process of oxidation a silver catalyst containing cadmium carbonate and/or cadmium oxide is employed along with fused alumina. Said additives prevent the agglomeration of the catalyst particles and decreases the silver content of the catalyst, reducing thereby the uneconomical consumption of silver. The cadmium carbonate and/or cadmium oxide introduced into the catalyst operating in a fluidized state serve to impart to the surface of silver a structure conducive to perfect fluidization of the catalyst and thus preventing both slugging and "dead zones". Over and above said components, the catalyst may also contain silver chloride which improves its selectivity.

The catalyst used in the process of ethylene oxidation is prepared in advance. If fused alumina is used as the filler, the relevant procedure is as follows.

Carbonates of silver and cadmium are precipitated from an aqueous solutions of their nitrates, using sodium carbonate. The precipitate so obtained is rinsed with water and dried at a temperature between 100° and 140° C. The powder of the carbonates of silver and cadmium is thoroughly mixed with powdered fused alumina having a particle size between 2 and 20 microns (the granulometric composition can be any within said limits). The mixture is pelletized under a pressure between 2000 and 4000 kg/cm$^2$, the pellets are crushed and screened using sieves with openings between 0.1 and 0.5 mm. The pellets of specified size are placed into a reactor. Before proceeding with the oxidation of ethylene, the carbonates are reduced in a stream of the reaction gas mixture at an elevated temperature which is that temperature of the oxidation process. At this stage, the silver carbonate is reduced to metallic silver and the cadmium carbonate is either not reduced at all or reduced to cadmium oxide partially or completely depending on the composition of the reaction gas mixture and the temperature of reduction.

For the purpose of improving the selectivity of the oxidation process, it is preferable to make use of a silver catalyst also containing, along with the components referred to above, silver chloride in an amount of between 0.03 and 0.1% of the weight of the silver present in the catalyst. To prepare a catalyst like this, a corresponding amount of hydrochloric acid or sodium chloride is added to the aqueous solution of sodium carbonate used in precipitating the carbonates of silver and cadmium.

If fused alumina is used as the support, the catalyst is prepared in the following way. First the support is prepared by pelletizing fused alumina powder having a particle size between 2 and 20 microns (the granulometric composition may be any within said limits) into porous pellets, using, for example, a taut oscillating gauze with openings of 0.1 mm. The pellets of regular round shape so obtained are calcinated in a furnace at a temperature between 1600° and 1650° C. for a period of 1 or 2 hours. When finished, the fused alumina support consists of pellets measuring 0.1 to 0.5 mm with a porosity of 25 to 45 vol % and a surface area between 0.2 and 0.8 m$^2$/g. The pores are of various size, predominantly within the range of 3000 to 15000 Å. Said characteristic features of the support can be controlled within the specified limits by changing the conditions of pelletizing, the temperature and the duration of calcination. In order to facilitate the pelletizing process and to add thereby the quality of support a 10- to 15-% aqueous solution of starch gum is preferably added to the pellet particles as a wetting agent. In this case the pelletizing can be accomplished in a disc pelletizer. The finished pellets are dried and calcinated at a temperature between 1600° and 1650° C. for a period lasting from 1 to 3 hours.

There is another method of preparing the fused alumina support consisting of pelletizing into porous pellets a mixture of fused alumina having a particle size of from 2 to 20 microns and glass, preferably a heat-resistant one, ground in advance in a ball mill to a particle size of between 5 and 40 microns. The fused alumina-to-glass ratio is between 3 and 10 to 1 parts by weight, respectively. The homogeneous mixture of powders is wetted with a 10- to 15-% aqueous solution of starch gum and is pelletized, by using, for example, a disc pelletizer. The pellets are dried and calcinated at a temperature of between 1200° and 1400° C. depending on the properties of the glass and the fused alumina-to-glass ratio. The properties of the pellets so obtained are within the limits specified hereinabove.

The fused alumina support prepared by either of the methods is impregnated with a composition, which is a suspension of carbonates of silver and cadmium in an aqueous solution of ethylene glycol, also prepared in advance. To that end, the carbonates of silver and cadmium are precipitated from an aqueous solution of their nitrates, using sodium carbonate. The precipitate so obtained is rinsed with water and suspended in a 20- to 70-% aqueous solution of ethylene glycol. The impregnation of the support with the suspension of carbonates of silver and cadmium is accomplished under the conditions of a gradual increase in the temperature up to between 60° and 100° C. The impregnated fused alumina support is dried at a temperature between 120° and 150° C. During the course of applying the carbonates to the fused alumina and drying the impregnated support, a reduction of the carbonates takes place. The function of ethylene glycol is two-fold. On one hand, the ethylene glycol behaves as a surfactant which reduces the surface tension of the suspension and facilitates the penetration of the active mass into the pores of the support. On the other hand, the ethylene glycol reduces the silver carbonate to metallic silver. At this stage, the carbonate of cadmium is either not reduced at all or is reduced to cadmium oxide partially or completely, depending on the temperature of the reduction and the amount of ethylene glycol present.

For the purpose of improving the selectivity of the process of ethylene oxidation, it is preferable to use a silver catalyst on a support also containing silver chloride in an amount between 0.1 and 0.3% of the weight of the silver present in the catalyst. A catalyst like this is prepared by introducing a corresponding amount of hydrochloric acid or sodium chloride into the aqueous solution of sodium carbonate used in precipitating the carbonates of silver and cadmium or by adding hydrochloric acid to an aqueous solution of ethylene glycol directly. The optimum amount of chlorine introduced into the catalyst composition is governed by the porosity of the support and the amount of silver present in the catalyst. The finished catalyst contains chlorine in the form of silver chloride.

The catalyst prepared in accordance with any of the methods disclosed hereinabove is placed in a reactor with a packing, said reactor being equipped with a gas distributing grid disposed in its lower part. The packing may be in the form of steel wire having multi-turn helices sized between 10×10 mm and 30×30 mm in length (the wire used is between 0.7 and 1.5 mm in diameter), and may be in the form of long multi-turn helices of variable diameter, a dense gauze or perforated rings, or single-turn helices. The packing improves the homogeneity of the fluidized bed, and prevents the passage of the reaction gas mixture through the catalyst bed in large bubbles interfering with both the mass and the heat transfer. The said packing creates in the catalyst bed conditions approaching those of ideal gas displacement and ideal mixing with the solid phase, i.e., with the catalyst. These factors add to the rate of reaction and improve the selectivity of the catalyst in operation. Uniform fluidization of the bed reduces the attrition of the catalyst.

If a large diameter reactor is used for the oxidation of ethylene in a fluidized bed of silver catalyst, it is preferable, for the sake of intensive removal of the heat of reaction, to use a reactor with cooling tubes, vertical tubes for example, with a packing disposed therebetween. The heat liberated during the reaction is removed mainly by circulating through said tubes a heat carrier which may be water boiling under pressure or an organic heat carrier. The packing providing for uniform fluidization of the catalyst bed may be embodied as specified hereinabove and disposed in the intertube space or, else, may have the form of longitudinal fins, slotted intricately-shaped plates or rods rigidly secured to the surface of the cooling tubes. In this latter case, i.e., when the packing is rigidly attached to the surface of tubes, it substantially extends the surface of heat transfer simultaneously with improving the state of fluidization. The size of the rods and the intricately-shaped plates, as well as the pattern of their disposition must be selected so as to ensure maximum filling of the space between the cooling tubes in order to prevent the formation of large gas bubbles without interfering, however, with an intensive intermixing of the catalyst particles. The intricately-shaped slotted plates may be secured to the surface of a cooling tube either along its axis or at an angle thereto. A checkerboard pattern of disposing the rods and the intricately-shaped plates on the surface of a tube may also be recommended. It is also expedient that the rods and the intricately shaped plates should alternate along the height of one tube with the rods and the intricately shaped plates of another tube. Such an arrangement of the packing counteracts the bubble-forming tendency of the gas mixture more effectively.

The two above-stated arrangements for the packing in the inter-tube space can be combined one with another so that, for example, longitudinal fins secured to the tube surface may be used in conjunction with multi-turn wire helices filling the space between the tubes.

In order to increase the selectivity of the catalyst and maintain it unchanged for a protracted period of service, it is preferable to oxidize ethylene in the presence of a chloride of sodium, potassium, lithium, barium or cadmium in the form of crystals measuring between 0.1 and 1 mm introduced into the fluidized bed of the silver catalyst in an amount between 0.1 and 5% of the weight of the silver present in the catalyst. As has been already mentioned hereinabove, to provide for a well-developed surface of chlorides and, consequently, for a pronounced increase in catalyst selectivity, it is preferable to apply said chlorides to a porous support which may be either fused alumina or Carborundum in pellets sized between 0.1 and 1 mm with a porosity of from 25 to 45 vol % and a surface area of 0.2 to 0.8 m$^2$/g. The chlorides are applied by impregnating the pellets of support in an aqueous solution of chlorides followed by the drying of pellets at a temperature between 100° and 150° C.

In order to promote catalyst selectivity and maintain it at a high level during a protracted period of service, it is better to dispose said chlorides (the chlorides of sodium, potassium, lithium, barium or cadmium) in a separate vessel in front of the reactor with the catalyst. The chlorides can be used in the form of crystals or they can be applied to a porous support which may be either fused alumina or Carborundum in pellets sized between 0.1 and 10 mm with a porosity of from 25 to 45 vol % and a surface area of 0.2 to 0.8 m$^2$/g. Said salts are used in an amount of between 0.5 and 5% of the weight of the silver present in the catalyst. In the case under consideration (chlorides in a separate vessel), the reaction gas mixture is passed through a bed of chlorides (on a support or without it) heated to between 100° and 300° C. in an amount of at least 1 vol %, i.e., partially or completely, preparatory to feeding said mixture into the fluidized bed of silver catalyst.

The advantage offered in this latter case (chlorides in a separate vessel) as compared with the preceding case (chlorides introduced into the fluidized bed directly) is the ability to control the selectivity of catalyst over a wider range by changing the temperature of the chloride bed and the amount of gas passed therethrough irrespectively of the conditions under which the oxidation of ethylene takes place.

Furthermore, to enhance the selectivity of catalyst and maintain it at a high level throughout a protracted period of service, some 0.1 to 1 vol % of the reaction gas mixture can be passed through a vessel (a bubble-type of scrubbing tower) containing pentachlorodiphenyl at a temperature of between 50° and 150° C. before feeding the said mixture into the fluidized bed of silver catalyst.

For the purpose of maintaining the oxygen content at the maximum tolerable explosion-proof level, increasing the yield of ethylene oxide and reducing the consumption of ethylene, it is preferable to oxidize ethylene in the presence of methane which may be added to the reaction gas stream in an amount as required to maintain the partial pressure of methane within the specified limits (0.5 to 10 atm) and to keep the ratio of the methane-to-ethylene partial pressure between 1:2 and 2:1, respectively.

The oxygen content of the reaction gas mixture may be increased the maximum tolerable explosion-proof level and raise the yield of ethylene oxide, by preferably adding more oxygen or air to the reaction gas mixture before feeding this mixture into the fluidized bed of silver catalyst. After the mixing with the additional amount of oxygen or air, the ethylene and oxygen content of the reaction gas mixture should not exceed the limits specified above (partial pressure of ethylene between 0.6 and 15 atm and that of oxygen between 0.1 and 2 atm). The said mixing takes place in the lower part of the reactor (below the fluidized bed of catalyst) where the vertical tubes and packing are disposed to provide for explosion-proof conditions for mixing the reaction gas mixture with the additional amount of oxygen or air.

When the vertical tubes are provided in the lower part of the reactor, the reaction gas mixture is passed through said tubes. They are given a small diameter, say between 5 to 30 mm, which provides for a rate of gas flow by far exceeding the speed of the flame propagation. An additional amount of oxygen or air introduced into the space between the tubes in the lower part of the reactor, passes through openings or nozzles provided in said tubes and enters the tubes mixing with the reaction gas mixture. The oxygen-enriched reaction gas mixture is fed to oxidation zone through said vertical tubes.

As has already been pointed out earlier, for the purpose of creating more hazard-proof conditions for mixing the reaction gas mixture with an extra amount of oxygen or air it is preferable to fill the vertical tubes and free space in the lower part of reactor with packing, i.e., the inter-tube space, the space between the tubes and the gas distributing grid and the space between the tubes and the bottom of the reactor. The packing may be of any kind, including beads, single and multi-turn helices, gauze rings of metal, fused alumina, Carborundum, ceramics and porcelain.

As pointed out hereinabove, the process of enriching the reaction gas mixture with oxygen can be accomplished in the lower part of the reactor filled with a packing in the form of beads, single and multi-turn helices, pellets and gauze rings. The reaction gas stream is fed into the bed of a packing at a rate of flow exceeding the speed of flame propagation. An additional amount of oxygen or air is introduced into the bed of packing through tubes, toroidal, for example, disposed in said bed of packing and provided with openings or nozzles. Upon passing through the bed of packing, the oxygen-enriched gas mixture is fed to the oxidation zone.

The present invention will be best understood from the following examples illustrating the method of producing ethylene oxide.

EXAMPLE 1

Ethylene was oxidized with oxygen on a silver catalyst prepared according to the following: in order to obtain 100 g of catalyst, 120.6 g of silver nitrate and 7.04 g of cadmium nitrate containing 2.56 g of cadmium metal were dissolved in 260 ml of distilled water. The solution of nitrates was slowly added to a boiling solution of 48.6 g of dehydrated sodium carbonate in 806 ml of distilled water. Preparatory to that, hydrochloric acid was added to the solution of sodium carbonate in an amount corresponding to a chlorine concentration of 0.01 or 0.02% of the weight of silver. The precipitation of salts was continued for a period of 30 to 40 minutes while stirring the solution continuously. The precipitate of carbonates of silver and cadmium and of silver chloride was rinsed with distilled water and dried at a temperature of 120° C. A mixture of said salts were added to the powder consisting of 18 g of dry and screened filler of fused alumina in pulverized form having a particle size between 8 and 20 microns. The powders were thoroughly mixed and pelletized under a pressure of between 2500 and 3000 kg/cm$^2$, the pellets were crushed and screened through a sieve with openings of between 0.1 and 0.5 mm. The pellets of the specified size (0.1 to 0.5 mm) were placed in a reactor provided with a packing. The packing was in the form of multi-turn helices having a diameter of 10 mm and a length of 10 mm made from steel wire 0.7 mm in diameter. The mixture of ethylene with oxygen fed for oxidation had a partial pressure for the ethylene of 1.7 atm, an oxygen partial pressure of 0.3 atm and an aggregate pressure of 2 atm. Preparatory to the process of ethylene oxidation, the silver carbonate was reduced to metallic silver (no reduction of cadmium carbonate took place) in the atmosphere of the reaction gas mixture under gradually increasing temperature conditions until the process temperature was attained in the reactor. The oxidation of ethylene was accomplished in a single pass-recycle system at a temperature of 240° C. and a space velocity of 3000 hr $^{-1}$ in a fluidized bed of a silver catalyst containing the components in the following proportion (wt.%): silver, 76; cadmium carbonate, 3.94; silver chloride, 0.06; fused alumina, 20. While carrying out the process of oxidation under said conditions, the ethylene oxide content in the gas mixture was 2.5 vol %, the hourly rate of output was 147 g of ethylene oxide per liter of catalyst and the selectivity was 65%.

EXAMPLE 2

The oxidation of ethylene was accomplished over a silver catalyst prepared as follows. In order to obtain 100 g of catalyst, 90.5 g of silver nitrate and 7.87 g of cadmium nitrate containing 2.86 g of cadmium metal were dissolved in 195 ml of distilled water. The solution of nitrates was slowly added to a boiling solution of 36.4 g of dehydrated sodium carbonate in 605 g of distilled water. The precipitation of the carbonates of silver and cadmium from the solution of their nitrates was continued for a period of 20 minutes under continuous stirring of the solution. The precipitate obtained was rinsed with distilled water and dried at a temperature of 140° C. 38.6 g of fused alumina filler having a particle size between 2 and 10 microns were added to the carbonate powder. The powders were throughly mixed, pelletized and the pellets were placed into a packed reactor where the reduction of silver carbonate to metallic silver on the lines as described in Example 1 was carried out as a preparation to the process of oxidation. Ethylene was oxidized under the same conditions as in Example 1, using a fluidized bed of a silver catalyst containing the components in the following proportion (wt %): silver, 57; cadmium carbonate, 4.4; fused alumina, 38.6. While carrying out the process of oxidation under said conditions, the ethylene oxide content in the gas mixture was 1.8 vol %, the hourly rate of output was 106 g of ethylene oxide per liter of catalyst and the selectivity was 61%.

EXAMPLE 3

The oxidation of ethylene with oxygen was carried out over a silver catalyst prepared in the following way. In order to obtain 100 g of catalyst, 31.6 g of silver nitrate and 2.88 g of cadmium nitrate containing 1.05 g of cadmium metal were dissolved in 68.5 ml of distilled water. The solution of nitrates was slowly added under the conditions of continuous stirring to a boiling solution of 12.6 g of dehydrated sodium carbonate in 212 ml of distilled water. The precipitation of the carbonates of silver and cadmium from the solution of their nitrates was accomplished within a period of 15 minutes under the conditions of continuous stirring. The precipitate thus obtained was rinsed with distilled water and added to a mixture composed of 33.3 ml of ethylene glycol and 13.3 ml of distilled water. The suspension of the carbonates of silver and cadmium in an aqueous solution of ethylene glycol was vigorously stirred and then 79 g of the porous fused alumina support in pellets sized between 0.1 and 0.5 mm having a porosity of 35 vol % and a surface area of 0.5 m$^2$/g were added to the suspension.

Said support had been prepared in advance by pelletizing the pulverized fused alumina having a particle size between 2 and 10 microns on a taut oscillating screen with an opening of 0.1 mm. The forces of adhesion coming into play had caused the minute particles of fused alumina to agglomerate into rolled pellets of regular shape. The pellets were calcinated in a furnace at 1650° C. for 2 hours.

The mixture of carbonates of silver and cadmium having a fused alumina support in an aqueous solution of ethylene glycol prepared as outlined above was vigorously agitated while heating to a temperature of 80° C. so as to apply said salts to the fused alumina and then the impregnated support was dried at a temperature of 150° C. for 8 hours. During the process of applying the carbonates to the fused alumina and the drying of the impregnated support, the silver carbonate was reduced to metallic silver and the cadmium carbonate to cadmium oxide with the aid of ethylene glycol. The catalyst so obtained had the following composition (wt.%): silver, 19.8; cadmium oxide, 1.2; fused alumina, 79. Upon separating the dust from the catalyst, the pellets sized between 0.1 and 0.5 mm were loaded into a reactor with a packing as described in Example 1. The stream of a mixture of ethylene and oxygen was fed for the oxidation process under a partial pressure of ethylene equal to 9 atm, that of oxygen amounting to 1 atm and under an aggregate pressure of 10 atm. The oxidation of ethylene was accomplished in a single pass-recycle system at a temperature of 220° C. and a space velocity of 3000 hr$^1$ in a fluidized bed of silver catalyst. While carrying out the process of oxidation under said conditions, the ethylene oxide content in the gas mixture was 3.3 vol %, the hourly rate of output was 198 g of ethylene oxide per liter of catalyst and the selectivity was 77.2%.

EXAMPLE 4

The oxidation of ethylene with oxygen was carried out over a silver catalyst prepared as follows. In order to obtain 100 g of catalyst, 15.8 g of silver nitrate and 1.45 g of cadmium nitrate containing 0.52 g of cadmium metal were dissolved in 35 ml of distilled water. Separately a solution was prepared containing 6.38 g of dehydrated sodium carbonate dissolved in 106 ml of distilled water. The solution of nitrates was slowly added under the conditions of continuous stirring to a boiling solution of sodium carbonate. The precipitate of the carbonates of silver and cadmium was rinsed with distilled water and added to a mixture consisting of 6.6 ml of ethylene glycol and 16.6 ml of distilled water. The suspension of carbonates in the aqueous solution of ethylene glycol was vigorously stirred and then 89.3 g of the porous fused alumina support were added having a pellet size between 0.1 and 0.5 mm, a porosity of 30 vol % and a specific surface area of 0.3 m$^2$/g.

Said support was prepared from fused alumina powder having a particle size between 5 and 10 microns, and from a heat-resistant glass ground in advance in a ball mill until its a particle size was 5 to 40 microns was reached. The powders of fused alumina and glass were mixed in a proportion of 4 to 1 in a Z-blade mixer for 2 hours, and then pelletized, using a disc pelletizer, under the conditions of wetting with a 15-% aqueous solution of starch gum. The pellets obtained were dried and calcinated at a temperature of 1300° C. for one hour.

The mixture of carbonates of silver and cadmium with a fused alumina support in an aqueous solution of ethylene glycol prepared as outlined above was vigorously agitated while heating to a temperature of 60° C. so as to apply said salts to said fused alumina, and then the impregnated support was dried at a temperature of 150° C. for 10 hours. During the process of applying the carbonates to the fused alumina and the drying of the impregnated support, the silver carbonate was reduced to metallic silver and the cadmium carbonate partially to cadmium oxide with the aid of ethylene glycol. The catalyst thus obtained had the following composition (wt.%): silver, 9.9; cadmium carbonate, 0.57; cadmium oxide, 0.17; fused alumina, 89.36. Upon separating the dust from the catalyst, the pellets sized between 0.1 and 0.5 mm were loaded into a reactor with a packing as described in Example 1. The stream of a mixture of ethylene and oxygen was fed for the oxidation process under a partial pressure of ethylene equal to 6.56 atm, that of oxygen amounting to 0.44 atm and under an aggregate pressure of 7 atm. The oxidation of ethylene was accomplished in a single pass-recycle system at a temperature of 220° C. and a space velocity of 3000 $hr^{-1}$ in a fluidized bed of silver catalyst. While carrying out the process of oxidation under said conditions, the ethylene oxide content in the gas mixture was 2.34 vol %, the hourly rate of output was 140 g of ethylene oxide per liter of catalyst and the selectivity was 67%.

EXAMPLE 5

The oxidation of ethylene with oxygen was carried out over a silver catalyst prepared as follows. In order to obtain 100 g of catalyst, 23.6 g of silver nitrate and 2.06 g of cadmium nitrate containing 0.75 g of cadmium metal were dissolved in 55 ml of distilled water. Separately a solution was prepared containing 9.5 g of dehydrated sodium carbonate dissolved in 160 ml of distilled water. The solution of nitrates was slowly added under the conditions of continuous stirring to a boiling solution of sodium carbonate. The precipitate of the carbonates of silver and cadmium so obtained was rinsed with distilled water and added to a mixture consisting of 25 ml of ethylene glycol and 10 ml of distilled water. The suspension of carbonates in the aqueous solution of ethylene glycol was vigorously stirred and then added to it were 84.31 g of a porous fused alumina support having a pellet size of from 0.1 to 0.5 mm, a porosity of 30 vol % and a specific surface area of 0.7 $m^2/g$.

Said support was prepared from fused alumina powder having a particle size between 10 and 20 microns, and using a disc pelletizer under the conditions of wetting the powder with a 10-% aqueous solution of starch gum applied by means of a sprayer. Minute particles of fused alumina were agglomerated into rolled pellets of regular shape. The pellets were dried and calcinated at a temperature of 1600° C. for 2 hours.

The mixture of carbonates of silver and cadmium with the fused alumina support in an aqueous solution of ethylene glycol prepared as outlined above was vigorously agitated for 1 hour, heated to 100° C. with a simultaneous stirring and dried at a temperature of 120° C. for 9 hours. During the heating step, the silver carbonate was reduced to metallic silver and the cadmium carbonate to cadmium oxide with the aid of ethylene glycol. The catalyst prepared in this way had the following composition (wt.%): silver, 14.9; cadmium oxide, 0.85; fused alumina, 84.25.

Upon separating the dust from the catalyst, the pellets sized between 0.1 and 0.5 mm were loaded into a reactor with a packing. The packing consisted of multi-turn helices with a diameter of 10 mm and a length of 10 mm made from steel wire 0.7 mm in diameter. Introduced into the bed of catalyst was sodium chloride applied to the same fused alumina support as was used in the preparation of catalyst. Sodium chloride was applied to the fused alumina by impregnating the fused alumina with an aqueous solution of sodium chloride followed by the drying of the impregnated support at a temperature of 120° C. The amount of the sodium chloride applied to the support was 0.2% of the weight of the silver present in the catalyst.

The stream of a mixture of ethylene and oxygen was fed into the reactor for the oxidation process under a partial pressure for ethylene equal to 4.48 atm, that for oxygen amounting to 0.52 atm and under an aggregate pressure of 5 atm. The oxidation of ethylene was accomplished in a single pass-recycle system at a temperature of 255° C. and a space velocity of 3000 $hr^{-1}$ in a fluidized bed of silver catalyst. While carrying out the process of oxidation under said conditions for a run lasting 1136 hours, the ethylene oxide content in the gas mixture was 3.54 vol %, the hourly rate of output was 206 g of ethylene oxide per liter of catalyst and the selectivity was 66.5%.

EXAMPLE 6

The oxidation of ethylene with oxygen was carried out in the same reactor and over the same catalyst as described in Example 5. Sodium chloride was introduced into the catalyst bed in the form of crystals between 0.25 and 0.5 mm in a total amount of 3.3% of the weight of the silver present in the catalyst. A mixture of ethylene and oxygen at a partial pressure for ethylene equal to 1.8 atm, that for oxygen amounting to 0.2 atm and at an aggregate pressure of 2 atms was introduced into the reactor. The oxidation of ethylene was accomplished in a single pass-recycle system at a temperature of 220° C. and a space velocity of 3000 $hr^{-1}$ in a fluidized bed of silver catalyst. While carrying out the process of oxidation under said conditions, the ethylene oxide content in the gas mixture was 4.1 vol %, the hourly rate of output was 200 g of ethylene oxide per liter of catalyst and the selectivity was 74.1%.

EXAMPLE 7

The oxidation of ethylene with oxygen was carried out using the same reactor and catalyst as described in Example 5. Lithium chloride applied to the same fused alumina support was added to the catalyst bed as the one used in the preparation of catalyst. Lithium chloride was applied to the fused alumina by impregnating the fused alumina with an aqueous solution of lithium chloride followed by the drying of an impregnated support at a temperature of 130° C. The content of the lithium chloride applied to the fused alumina was 0.21% of the weight of the silver present in the catalyst.

A mixture of ethylene with oxygen was fed to the oxidation process at a partial pressure for ethylene equal to 1.66 atm, that for oxygen amounting to 0.34 atm and at an aggregate pressure of 2 atm. The oxidation of ethylene was accomplished in a single pass-recycle system at a temperature of 240° C. and at a space velocity of 2000 hr$^{-1}$ in a fluidized bed of silver catalyst. While carrying out the process of oxidation under said conditions, the ethylene oxide content in the gas mixture was 5.14 vol %, the hourly rate of output was 279 g of ethylene oxide per liter of catalyst and the selectivity was 67.5%.

Identical results were obtained when potassium chloride applied to a fused alumina support had been introduced into the catalyst bed in an amount of 0.54% of the weight of silver.

EXAMPLE 8

The oxidation of ethylene with oxygen was accomplished in of the same reactor and with the same catalyst as described in Example 5. Cadmium chloride was introduced into the catalyst bed applied to the same fused alumina support as the one used in the preparation of the catalyst. Cadmium chloride was applied to fused alumina by impregnating the fused alumina with an aqueous solution of cadmium chloride followed by drying the impregnated support at a temperature of 120° C. The content of the cadmium chloride applied to fused alumina was 0.54% of the weight of the silver present in the catalyst.

A mixture of ethylene with oxygen was fed to the oxidation stage at a partial pressure for ethylene equal to 1.66 atm, that for oxygen amounting to 0.34 atm and at an aggregate pressure of 2 atm. The oxidation of ethylene was accomplished in a single pass-recycle system at a temperature of 260° C. and a space velocity of 2000 hr$^{-1}$ in a fluidized bed of silver catalyst. While carrying out the process of oxidation under said conditions, the ethylene oxide content in the gas mixture was 5.2 vol %, the hourly rate of output was 284 g of ethylene oxide per liter of catalyst and the selectivity was 67.9%.

EXAMPLE 9

The oxidation of ethylene with oxygen was accomplished in the same reactor and catalyst as described in Example 5. Barium chloride was introduced into the catalyst bed applied to the same fused alumina support as the one used in the preparation of the catalyst. Barium chloride was applied to fused alumina by impregnating the fused alumina with an aqueous solution of barium chloride followed by drying the impregnated support at a temperature of 110° C. The content of the barium chloride applied to fused alumina was 0.1% of the weight of the silver present in the catalyst.

In the mixture of ethylene with oxygen fed for oxidation, the partial pressure for ethylene was 1.75 atm, that for oxygen reached 0.25 atm and the aggregate pressure of the mixture was 2 atm. The oxidation of ethylene took place in a single pass-recycle system at a temperature of 230° C. and at a space velocity of 2000 hr$^{-1}$ in a fluidized bed of silver catalyst. While carrying out the process of oxidation under said conditions, the ethylene oxide content in the gas mixture was 3.9 vol %, the hourly rate of output was 203 g of ethylene oxide per liter of catalyst and the selectivity was 67.5%.

EXAMPLE 10

The oxidation of ethylene with oxygen took place in a single pass-recycle system, using the same reactor and catalyst as described in Example 5. A separate vessel arranged before the reactor with the catalyst was charged with sodium chloride applied to the same fused alumina support as the one used in the preparation of the catalyst. Sodium chloride was applied to fused alumina by impregnating the fused alumina with an aqueous solution of sodium chloride followed by drying the impregnated support at a temperature of 120° C. The content of the sodium chloride applied to the fused alumina was 5% of the weight of the silver present in the catalyst.

The mixture of ethylene and oxygen being fed for oxidation, of which the partial pressure of ethylene was 1.78 atm, that of oxygen reached 0.22 atm, while the aggregate pressure of the mixture was 2 atm. The oxidation of ethylene was accomplished at a temperature of 240° C. and a space velocity of 3000 hr$^{-1}$ in a fluidized bed of silver catalyst. Some of the circulating gas stream in an amount of 1 vol % was passed in succession through a bed of sodium chloride applied to a fused alumina support, heated to a temperature of 260° C. and disposed in a separate vessel and through the reactor with the catalyst. In conducting the process of ethylene oxidation under said conditions, the ethylene oxide content in the gas mixture was 4.2 vol %, the hourly rate of output was 218 g of ethylene oxide per liter of catalyst and the selectivity was 68.3%.

EXAMPLE 11

The catalyst was prepared on the lines as described in Example 3, the only difference being that hydrochloric acid containing chlorine in an amount corresponding to 0.05% of the weight of silver had been added to the solution of anhydrous sodium carbonate used in precipitating the carbonates of silver and cadmium. The catalyst so obtained was of the following composition (wt %): silver, 19.8; cadmium oxide, 1.2; silver chloride, 0.04; fused alumina, 78.96. The catalyst was loaded into a reactor with packing composed of multi-turn helices having a diameter of 10 mm and a length of 10 mm made from steel wire 0.7 mm in diameter.

The mixture of ethylene and oxygen fed for oxidation had a partial pressure for ethylene and oxygen of 4.4 and 0.6 atm, respectively, while the aggregate pressure was 5 atm. The oxidation of ethylene took place in a single pass-recycle system at a temperature of 260° C. and a space velocity of 3000 hr$^{-1}$ in a fluidized bed of silver catalyst. In conducting the process of ethylene oxidation under said conditions, the ethylene content in the gas mixture was 4.7 vol %, the hourly rate of output was 294 g of ethylene oxide per liter of catalyst and the selectivity was 70%.

EXAMPLE 12

The process of oxidizing ethylene with oxygen was accomplished in a reactor with a diameter of 180 mm accomodating three vertical cooling tubes 32 mm in diameter with water boiling under pressure circulating therethrough. The reactor was filled with a packing consisting of steel rods having a diameter of 3 mm and 24 mm long which had been welded to the surface of tubes. The rods on each tube were disposed in groups spaced 12 mm apart and each containing 12 rods fitted all the way around the circumference of the tube and staggered at 15 degrees with respect to the rods in the preceding group. Furthermore, the rods along one tube alternated with their opposite numbers along another tube. The said reactor was filled with a catalyst prepared as outlined in Example 5 except that the size of the pellets was between 0.25 and 0.5 mm. Sodium chloride added to the bed of catalyst, was applied to the same fused alumina support as the one used in preparing the catalyst. Sodium chloride was applied to fused alumina by impregnating fused alumina with an aqueous solution of sodium chloride followed by drying the impregnated support at a temperature of 120° C. The content of the chloride applied to fused alumina was 5% of the weight of the silver present in the catalyst.

The oxidation of ethylene took place in a circulating system at a temperature of 250° C. and a space velocity of 4200 hr$^{-1}$ in a fluidized bed of silver catalyst at an aggregate pressure of 6 atm. The reaction gas mixture contained ethylene and oxygen in amounts which had provided for a partial pressure of ethylene and oxygen equal to 4.2 and 0.53 atm, respectively, the balance being non-reactants (carbon dioxide, nitrogen, argon, methane, water vapours). In conducting the process of oxidation under said conditions, the ethylene oxide content in the gas mixture was 2.8 vol %, the hourly rate of the output was 230 g of ethylene oxide and the selectivity was 67%.

Similar results were obtained during the oxidation under the same conditions but using a reactor 120 mm in diameter with two vertical cooling tubes 25 mm in diameter, said tubes being provided with longitudinal fins 8 mm high welded to the surface of the tubes. The inter-tube space was filled with a packing in the form of multi-turn helices 20 mm in diameter and 20 mm long made of steel wire 1 mm in diameter.

In a reactor not provided with any of said types of packing but incorporating vertical cooling tubes, the process was conducted with the ethylene content in the gas mixture being equal to 1.6 vol %, an hourly rate of output amounting to 130 g of ethylene oxide per liter of catalyst and with a selectivity of 59%, other factors being equal.

EXAMPLE 13

The process of oxidizing ethylene with oxygen was accomplished in a reactor with a diameter of 120 m accomodating two vertical cooling tubes 25 mm in diameter with water boiling under pressure circulating therethrough. The tubes were provided with a packing in the form of longitudinal steel fins 8 mm high welded to the surface of tubes. The inter-tube space was filled with a packing composed of multi-turn helices 20 mm long and with a diameter of 20 mm made of steel wire 1 mm in diameter. Said reactor was charged with a catalyst prepared as described in Example 5 consisting of pellets between 0.25 and 0.5 mm containing 0.2 wt. % of silver chloride.

The oxidation of ethylene took place in a circulating system at a temperature of 245° to 250° C., a space velocity of 4000 hr$^{-1}$ under an aggregate pressure of 9 atm in a fluidized bed of silver catalyst. The partial pressure of the ethylene and oxygen contained in the reaction gas mixture was 5.8 to 6.3 atm and 0.65 to 0.7 atm, respectively, the balance being non-reactants (carbon dioxide, nitrogen, argon, methane, water vapours). In order to improve the selectivity of the catalyst, some of the reaction gas mixture in an amount of 1 vol % was passed through a vessel containing pentachlorodiphenyl heated to a temperature of 120° C. before being admitted into the reactor with the catalyst. After conducting the process of oxidation under said conditions for a period of 400 hours, the ethylene oxide content in the gas mixture was 2.7 or 2.8 vol %, the hourly rate of output varied between 200 and 215 g of ethylene oxide per liter of catalyst and the selectivity was 68 to 70%.

EXAMPLE 14

The oxidation of ethylene with air was accomplished in a reactor 120 mm in diameter containing two vertical cooling tubes 25 mm in diameter circulating through which was water boiling under pressure. The inter-tube space was filled with a packing composed of multi-turn helices having a diameter of 20 mm and 20 mm in length made from steel wire 1 mm in diameter. Said reactor was charged with a catalyst prepared as described in Example 5, the pellets having a size of 0.25 to 0.5 mm and containing 0.2 wt. % of silver chloride.

The oxidation of ethylene took place in a circulating system at a temperature of 252° C., a space velocity of 6400 hr$^{-1}$ under an aggregate pressure of 15 atm in a fluidized bed of silver catalyst. The partial pressure of ethylene and oxygen contained in the reaction gas mixture was 0.6 and 0.92 atm, respectively, the balance being non-reactants (carbon dioxide, nitrogen, argon, methane, water vapours). After conducting the process of oxidation under said conditions, the ethylene oxide content in the gas mixture was 1 vol %, the hourly rate of output amounted to 125 g of ethylene oxide per liter of catalyst and the selectivity was 69%.

EXAMPLE 15

The oxidation of ethylene with air was accomplished in a reactor 120 mm in diameter containing two vertical cooling tubes 25 mm in diameter circulating through which was water boiling under pressure. The tubes were provided with a packing composed of longitudinal steel fins 8 mm high welded to the surface of the tubes. The inter-tube space was filled with a packing composed of multi-turn helices having a diameter of 10 mm and a length of 10 mm made from steel wire 1 mm in diameter. Said reactor was charged with a catalyst prepared as described in Example 5, the pellets being 0.25 to 0.5 mm in size and containing 0.16 wt. % of silver chloride.

The oxidation of ethylene took place in a circulating system at a temperature of 242° to 248° C., a space velocity between 4000 and 4100 hr$^{-1}$ under an aggregate pressure of 11 atm in a fluidized bed of silver catalyst. The partial pressure of ethylene and oxygen contained in the reaction gas mixture was 8.1 to 8.8 atm and 0.66 to 0.75 atm, respectively, the balance being non-reactants (carbon dioxide, nitrogen, argon, methane, water vapours). In order to improve the selectivity of the catalyst, some of the reaction gas mixture in an amount of 0.5 vol % was passed through a vessel containing pentachloridiphenyl heated to a temperature of 130° C. being being admitted into the reactor with catalyst. After conducting the process of oxidation under said conditions for a period of 300 hours, the ethylene oxide content in the gas mixture was 2.25 to 2.35 vol %, the hourly rate of output varied between 180 and 190 g of ethylene oxide per liter of catalyst and the selectivity was 69%.

Identical results were obtained under the same conditions of oxidation in a 120-mm reactor with two vertical fin-less cooling tubes 25 mm in diameter and the same helical packing filling the space therebetween.

EXAMPLE 16

The process of oxidizing ethylene with oxygen took place under the same conditions and using the same reactor as described in Example 15. The only difference was that an additional amount of oxygen had been introduced into the reaction gas mixture before feeding this into the fluidized bed of silver catalyst. This mixing was accomplished in the lower part of the reactor (below the fluidized bed of catalyst) where seven vertical tubes having a bore of 5 mm were provided. Flowing through said tubes was the reaction gas mixture and admitted into the inter-tube space in the lower part of the reactor was an additional amount of oxygen which, entering said tubes through holes provided therein, was mixed with the reaction gas mixture. The oxygen-rich reaction gas mixture was fed to the oxidation stage through the vertical tubes. The partial pressure of the oxygen in the reaction gas mixture was 0.66 to 0.75 atm before the introduction of additional oxygen and 0.83 to 1 atm after. As a result, the ethylene oxide content in the gas mixture was 2.65 to 2.8 vol %, the hourly rate of output was 205 to 220 g of ethylene oxide per liter of catalyst and the selectivity was 68 to 69% for a period of 300 hours when the catalyst was in service.

EXAMPLE 17

The process of oxidizing ethylene with oxygen was accomplished in a reactor with a diameter of 120 mm accomodating two vertical cooling tubes with a diameter of 25 mm. Water boiling under pressure was passed through said tubes. The inter-tube space was filled with multi-turn helices 20 mm in diameter and 20 mm in length made from steel wire 1 mm in diameter. Said reactor was charged with a catalyst prepared as outlined in Example 5, but consisting of pellets between 0.25 and 0.5 mm with a silver chloride content of 0.24 wt. %.

The oxidation of ethylene took place in a circulating system at a temperature of 238° C. and a space velocity of 4100 hr$^{-1}$ in a fluidized bed of silver catalyst. The process of oxidation was accomplished in the presence of methane introduced into the circulating reaction gas mixture before the reactor. The reaction gas mixture under an aggregate pressure of 11 atm contained ethylene, methane and oxygen at a partial pressure of 4.4, 4.6 and 0.81 atm, respectively, the balance being non-reactants (carbon dioxide, nitrogen, argon, water vapours). In conducting the process of oxidation under said conditions, the ethylene oxide content in the gas mixture was 2.62 vol %, the hourly rate of output reached 210 g of ethylene oxide per liter of catalyst and the selectivity was 69%.

What is claimed is:

1. A method of producing ethylene oxide with an oxidizing agent selected from the group consisting of molecular oxygen and air, in a reactor having a fluidized bed of a silver catalyst therein consisting essentially of from 9.5 to 19 wt. % of metallic silver; from 0.5 to 1 wt. % of a cadmium compound selected from the group consisting of cadmium carbonate, cadmium oxide, and mixtures thereof, said wt. % of both the silver and cadmium components being based on continuously reacting ethylene on a single pass-recycle basis with said oxidizing agent at a temperature of from 200° to 300° C. at a partial pressure of oxygen of from 0.1 to 2 atm., and at a partial pressure of ethylene of from 0.6 to 15 atm., and an aggregate pressure of from 2 to 20 atm., said catalyst being prepared by precipitating carbonate salts of silver and cadmium; impregnating same into a porous fused alumina carrier having a particle size of from 0.1 to 0.5 mm with a porosity of from 25 to 45 vol. % and a specific surface area of from 0.2 to 0.8 M$^2$/gm in an 20-70% aqueous solution of ethylene glycol while gradually increasing the temperature up to between 60° and 100° C.; and drying said impregnated alumina carrier with heating at a temperature of from 120° to 150° C., the silver component of said catalyst being reduced to metallic silver during the impregnating and drying steps.

2. The method according to claim 1, wherein the oxidation of ethylene is carried out in a reactor having cooling tubes therein and including non-fluidizable packing, said packing being disposed in the space between said cooling tubes in the reactor.

3. The method according to claim 1, wherein the silver catalyst also contains silver chloride prepared by co-precipitation in an amount of from 0.1 to 0.3% of the weight of the total silver present in the catalyst.

4. The method according to claim 1, wherein the reaction gas mixture, before being fed into the fluidized bed of a silver catalyst, is passed in an amount of at least 1, vol % through a bed of a chloride of a metal selected from the group consisting of sodium, potassium, lithium, barium and cadmium heated to a temperature between 100° and 300° C. with the metal chloride being used in an amount of from 0.5 to 5% of the weight of the silver present in the catalyst.

5. The method according to claim 4, wherein chlorides are applied to a porous support and used in pellets sized from 0.1 to 10 mm, having a porosity of from 25 to 45 vol % and a specific surface area of from 0.2 to 0.8 m$^2$/g.

6. The method according to claim 1, wherein the reaction gas mixture before being fed into the fluidized bed of a silver catalyst is passed in an amount of from 0.1 to 1 vol % through pentachlorodiphenyl at a temperature of from 50° to 150° C.

7. The method according to claim 2, wherein the reaction gas mixture before being fed into the fluidized bed of a silver catalyst is passed in an amount of from 0.1 to 1 vol % through pentachlorodiphenyl at a temperature of from 50° to 150° C.

8. The method according to claim 3, wherein the reaction gas mixture before being fed into the fluidized bed of a silver catalyst is passed in an amount of from 0.1 to 1 vol % through pentachlorodiphenyl at a temperature of from 50° to 150° C.

9. The method according to claim 1, wherein the reaction gas mixture consisting essentially of ethylene and an oxidizing agent, before being fed into the fluidized bed of said silver catalyst, is mixed with a further quantity of an oxidizing agent selected from the group consisting of oxygen and air, with the mixing taking place in vertical tubes disposed in the lower part of said reactor said tubes being sized to provide explosion-proof conditions for the mixing of said gases.

10. The method according to claim 9, wherein the vertical tubes and the free space in the lower part of the reactor are filled with a non-fluidizable packing.

11. The method according to claim 2, wherein the reaction gas mixture consisting essentially of ethylene and an oxidizing agent, before being fed into the fluidized bed of said silver catalyst, is mixed with a further quantity of an oxidizing agent selected from the group consisting of oxygen and air, with the mixture taking place in the vertical tubes disposed in the lower part of said reactor, said tubes being sized to provide explosion-proof conditions for the mixing of said gases.

12. The method according to claim 11, wherein the vertical tubes and the free space in the lower part of the reactor are filled with a non-fluidizable packing.

13. The method according to claim 3, wherein the reaction gas mixture consisting essentially of ethylene and an oxidizing agent, before being fed into the fluidized bed of said silver catalyst, is mixed with a further quantity of an oxidizing agent selected from the group consisting of oxygen and air, said mixing taking place in the vertical tubes disposed in the lower part of said reactor, said tubes being sized to provide explosion-proof conditions for the mixing of said gases.

14. The method according to claim 13, wherein the vertical tubes and the free space in the lower part of the reactor are filled with a non-fluidizable packing.

15. The method according to claim 1, wherein the reaction gas mixture consisting essentially of ethylene and an oxidizing agent, before being fed into the fluidized bed of said silver catalyst, is mixed with a further quantity of an oxidizing agent selected from the group consisting of oxygen and air, with the mixing taking place in a bed of a non-fluidizable packing filling the lower part of said reactor and said reaction gas mixture being fed into said bed at a rate of flow exceeding the speed of flame propagation to assure explosion-proof conditions for the mixing of said gases.

16. The method according to claim 2, wherein the reaction gas mixture consisting essentially of ethylene and an oxidizing agent, before being fed into the fluidized bed of said silver catalyst, is mixed with a further quantity of an oxidizing agent selected from the group consisting of oxygen and air, with the mixing taking place in a bed of a non-fluidizable packing filling the lower part of said reactor and said reaction gas mixture being fed into said bed at a rate of flow exceeding the speed of flame propagation to assure explosion-proof conditions for the mixing of said gases.

17. The method according to claim 3, wherein the reaction gas mixture consisting essentially of ethylene and an oxidizing agent, before being fed into the fluidized bed of a silver catalyst, is mixed with a further quantity of an oxidizing agent selected from the group consisting of oxygen and air, with the mixing taking place in a bed of a non-fluidizable packing filling the lower part of said reactor and said reaction gas mixture being fed into said bed at a rate of flow exceeding the speed of flame propagation to assure explosion-proof conditions for the mixing of said gases.

* * * * *